United States Patent
Roberts

(10) Patent No.: US 6,390,886 B1
(45) Date of Patent: May 21, 2002

(54) NURSING PAD

(76) Inventor: Cathy G. Roberts, 1402 E. Wilson Ave., Escondido, CA (US) 92027

( * ) Notice: Subject to any disclaimer, the term of this patent is extended or adjusted under 35 U.S.C. 154(b) by 0 days.

(21) Appl. No.: 09/876,950

(22) Filed: Jun. 8, 2001

(51) Int. Cl.[7] ............................................. A41D 27/12
(52) U.S. Cl. ............................................. 450/37; 2/57
(58) Field of Search ............................. 450/37, 38, 39, 450/57, 55; 2/267, 268; 128/890; 602/60, 61

(56) References Cited

U.S. PATENT DOCUMENTS

| | | | |
|---|---|---|---|
| 2,627,606 A | * 2/1953 | De Grandes | 450/57 |
| 2,891,544 A | * 6/1959 | London | 450/57 |
| 2,925,816 A | * 2/1960 | Rosenthal | 450/57 |
| RE26,790 E | * 2/1970 | Silverman | 450/37 |
| 3,600,717 A | * 8/1971 | McKeehan | 36/9 A |
| 4,047,534 A | 9/1977 | Thomaschefsky | |
| 4,074,721 A | * 2/1978 | Smits et al. | 450/57 |
| 4,125,114 A | 11/1978 | Repke | |
| 4,164,228 A | * 8/1979 | Weber-Unger | 450/57 |
| 4,590,931 A | * 5/1986 | Kidwell, Jr. | 2/400 |
| 4,674,131 A | * 6/1987 | Broel | 2/53 |
| 5,017,174 A | * 5/1991 | Gowrylow | 450/57 |
| 5,149,336 A | 9/1992 | Clarke et al. | |
| D347,278 S | 5/1994 | Higa | |
| 5,690,536 A | * 11/1997 | Madden et al. | 450/37 |
| 6,036,577 A | 3/2000 | Coburn | |
| 6,074,272 A | * 6/2000 | Hebert | 450/37 |
| 6,080,139 A | * 6/2000 | Gallegos | 2/1 |

* cited by examiner

*Primary Examiner*—Gloria M. Hale

(57) ABSTRACT

A nursing pad for positioning over a lactating breast. The nursing pad includes a panel having outer layer and an inner layer. The outer layer has a generally convex shape and the inner layer has a generally concave shape. The outer layer comprises a generally water impermeable flexible material. The inner layer comprises an absorbent material. The panel has a peripheral edge having a slot therein. The slot extends toward a central area of the panel and is defined by a first and second oppositely located edge. A securing member removably secures the first edge in close proximity to the second edge.

9 Claims, 1 Drawing Sheet

NURSING PAD

BACKGROUND OF THE INVENTION

1. Field of the Invention

The present invention relates to nursing pad devices and more particularly pertains to a new nursing pad for positioning over a lactating breast.

2. Description of the Prior Art

The use of nursing pad devices is known in the prior art. More specifically, nursing pad devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 6,036,577; 5,149,336; 4,125,114; 4,047,534; 4,074,721; and U.S. Pat. No. Des. 347,278.

While these devices fulfill their respective, particular objectives and requirements, the aforementioned patents do not disclose a new nursing pad. The inventive device includes a panel having outer layer and an inner layer. The outer layer has a generally convex shape and the inner layer has a generally concave shape. The outer layer comprises a generally water impermeable flexible material. The inner layer comprises an absorbent material. The panel has a peripheral edge having a slot therein. The slot extends toward a central area of the panel and is defined by a first and second oppositely located edge. A securing member removably secures the first edge in close proximity to the second edge.

In these respects, the nursing pad according to the present invention substantially departs from the conventional concepts and designs of the prior art, and in so doing provides an apparatus primarily developed for the purpose of positioning over a lactating breast.

SUMMARY OF THE INVENTION

In view of the foregoing disadvantages inherent in the known types of nursing pad devices now present in the prior art, the present invention provides a new nursing pad construction wherein the same can be utilized for positioning over a lactating breast.

The general purpose of the present invention, which will be described subsequently in greater detail, is to provide a new nursing pad apparatus and method which has many of the advantages of the nursing pad devices mentioned heretofore and many novel features that result in a new nursing pad which is not anticipated, rendered obvious, suggested, or even implied by any of the prior art nursing pad devices, either alone or in any combination thereof.

To attain this, the present invention generally comprises a panel having outer layer and an inner layer. The outer layer has a generally convex shape and the inner layer has a generally concave shape. The outer layer comprises a generally water impermeable flexible material. The inner layer comprises an absorbent material. The panel has a peripheral edge having a slot therein. The slot extends toward a central area of the panel and is defined by a first and second oppositely located edge. A securing member removably secures the first edge in close proximity to the second edge.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nursing pad apparatus and method which has many of the advantages of the nursing pad devices mentioned heretofore and many novel features that result in a new nursing pad which is not anticipated, rendered obvious, suggested, or even implied by any of the prior art nursing pad devices, either alone or in any combination thereof.

It is another object of the present invention to provide a new nursing pad which may be easily and efficiently manufactured and marketed.

It is a further object of the present invention to provide a new nursing pad which is of a durable and reliable construction.

An even further object of the present invention is to provide a new nursing pad which is susceptible of a low cost of manufacture with regard to both materials and labor, and which accordingly is then susceptible of low prices of sale to the consuming public, thereby making such nursing pad economically available to the buying public.

Still yet another object of the present invention is to provide a new nursing pad which provides in the apparatuses and methods of the prior art some of the advantages thereof, while simultaneously overcoming some of the disadvantages normally associated therewith.

Still another object of the present invention is to provide a new nursing pad for positioning over a lactating breast.

Yet another object of the present invention is to provide a new nursing pad which includes a panel having outer layer and an inner layer. The outer layer has a generally convex shape and the inner layer has a generally concave shape. The outer layer comprises a generally water impermeable flexible material. The inner layer comprises an absorbent material. The panel has a peripheral edge having a slot therein. The slot extends toward a central area of the panel and is defined by a first and second oppositely located edge. A securing member removably secures the first edge in close proximity to the second edge.

Still yet another object of the present invention is to provide a new nursing pad that has a slot therein for adjusting to variable sized breasts.

Even still another object of the present invention is to provide a new nursing pad that has an elastic band thereon for preventing leakage around the panel.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
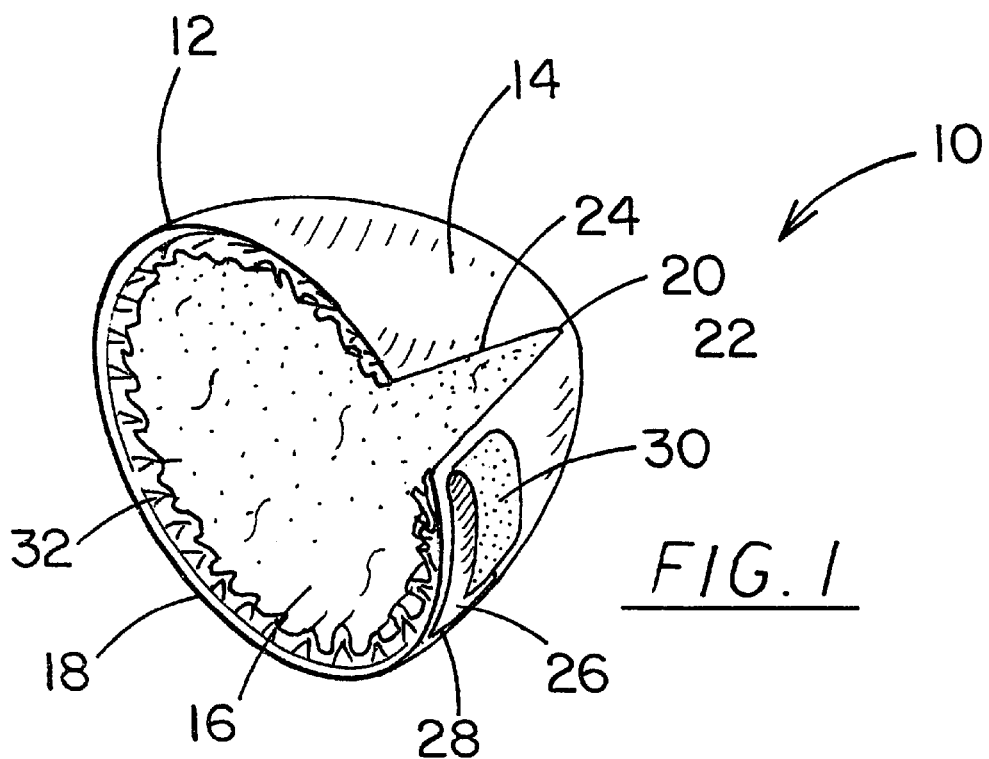
FIG. 1 is a schematic perspective view of a new nursing pad according to the present invention.
Figure 2:
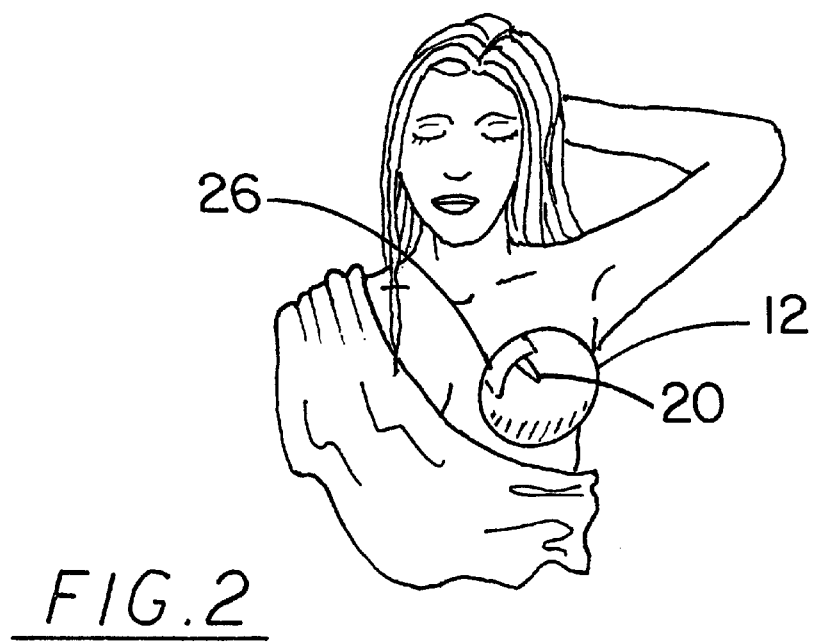
FIG. 2 is a schematic front in-use view of the present invention.

With reference now to the drawings, and in particular to FIGS. 1 and 2 thereof, a new nursing pad embodying the principles and concepts of the present invention and generally designated by the reference numeral 10 will be described.

As best illustrated in FIGS. 1 and 2, the nursing pad 10 generally comprises a panel 12 having outer layer 14 and an inner layer 16. The outer layer 14 has a generally convex shape and the inner layer 16 has a generally concave shape. The outer layer 14 comprises a flexible material. The outer layer 14 is generally water impermeable and ideally comprises a plastic material. The inner layer 16 comprises an absorbent material such as cellulose fiber material or a cotton material. The absorbent material is resiliently flexible such that the inner layer 16 achieves a cushioning effect when the panel is positioned on a breast. The panel 12 has a peripheral edge 18 having a slot 20 therein extending toward a central area of the panel 12 defined by a first 22 and second 24 oppositely located edge.

A securing member 26 removably secures the first edge 22 in close proximity to the second edge 24. The securing member 26 comprises a strap having a first edge 28 coupled to the outer layer 14 and positioned generally adjacent to the first edge 22. The strap, or securing member 26, extends toward the second edge 24. A pressure sensitive adhesive 30 generally coats a bottom surface of the strap 26. Alternatively, a hook and loop fastener may be used instead of adhesive. The bottom surface may be removably adhered to the outer layer 14 adjacent to the second edge 24.

An elastic band 32 is attached to and extends along the peripheral edge 18 of the panel 12.

In use, the inner layer 16 of the panel 12 is positioned against a lactating breast to prevent leakage and staining on the clothes of a nursing mother. The slot 20 allows for some variation in the size of the panel for variable sized breasts within a certain range. To accommodate larger differences in ranges of size, the device 10 would be made in sizes to comport with brazier cup sizes such as A, B, C, D and DD, while the slot 20 would allow the size to be altered with only slight variation outside of the standard cup sizes. The elastic band 32 offers a snug fit around the entire breast to provide comfort and prevent leakage.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nursing pad device for positioning over the breast of a user, said device comprising:

a panel having outer layer and an inner layer, said outer layer having a generally convex shape and said inner layer having a generally concave shape, said outer layer comprising generally water impermeable flexible material, said inner layer comprising an absorbent material, said panel having a peripheral edge having a slot therein, said slot extending toward a central area of said panel and being defined by a first and second oppositely located edge; and a securing member removably secures said first edge in close proximity to said second edge, said securing member comprising a strap having a first edge coupled to said outer layer and positioned generally adjacent to said first edge, said strap extending toward said second edge, a pressure sensitive adhesive generally coating a bottom surface of said strap, wherein said bottom surface may be removably adhered to said outer layer adjacent to said second edge.

2. The nursing, pad device as in claim 1, wherein said absorbent material is resiliently flexible such that a cushioning effect is achieved by said inner layer.

3. The nursing pad device as in claim 1, further including an elastic band being attached to and extending along said peripheral edge of said panel.

4. A nursing pad device for positioning over the breast of a user, said device comprising:

a panel having an outer layer and an inner layer, said outer layer having a generally convex shape and said inner layer having a generally concave shape, said outer layer comprising a flexible material, said outer layer being generally water impermeable and comprising a plastic material, said inner layer comprising an absorbent material, said absorbent material being resiliently flexible such that a cushioning effect is achieved by said inner layer, said panel having a peripheral edge having a slot therein, said slot extending toward a central area of said panel and being defined by a first and second oppositely located edge;

a securing member for removably securing said first edge in close proximity to said second edge, said securing member comprising a strap having a first edge coupled to said outer layer and positioned generally adjacent to said first edge, said strap extending toward said second edge, a pressure sensitive adhesive generally coating a bottom surface of said strap, wherein said bottom surface may be removably adhered to said outer layer adjacent to said second edge; and an elastic band being attached to and extending along said peripheral edge of said panel.

5. A nursing pad device for positioning over the breast of a user, said device comprising:

a panel having outer layer and an inner layer, said outer layer having a generally convex shape and said inner layer having a generally concave shape said panel having a peripheral edge having a slot therein, said slot extending toward a central area of said panel and being defined by a first and second oppositely located edge; and a securing member removably secures said first edge in close proximity to said second edge, said securing member comprising a strap having a first edge coupled to said outer layer and positioned generally adjacent to said first edge, said strap extending toward said second edge, a fastening means releasably fastens a bottom surface of said strap to said outer layer adjacent to said second edge.

6. The nursing pad device as in claim 5, wherein said outer layer comprises a generally water impermeable flexible material and said inner layer comprises an absorbent material.

7. The nursing pad device as in claim 5, wherein said fastening means comprises a pressure sensitive adhesive generally covering said bottom side of said strap.

8. The nursing pad device as in claim 6 wherein said absorbent material is resiliently flexible such that a cushioning effect is achieved by said inner layer.

9. The nursing pad device as in claim 5, further including an elastic band being attached to and extending along said peripheral edge of said panel.

* * * * *